United States Patent
Ichiki

(10) Patent No.: US 10,058,237 B2
(45) Date of Patent: Aug. 28, 2018

(54) IMAGE PROCESSING DEVICE, IMAGE PROCESSING METHOD, AND PROGRAM

(71) Applicant: Sony Corporation, Tokyo (JP)

(72) Inventor: Hiroshi Ichiki, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 14/625,090

(22) Filed: Feb. 18, 2015

(65) Prior Publication Data

US 2015/0243027 A1    Aug. 27, 2015

(30) Foreign Application Priority Data

Feb. 24, 2014 (JP) ................ 2014-032808

(51) Int. Cl.
| | |
|---|---|
| *G06K 9/00* | (2006.01) |
| *A61B 1/04* | (2006.01) |
| *G06K 9/46* | (2006.01) |
| *A61B 1/00* | (2006.01) |
| *G06T 7/13* | (2017.01) |

(52) U.S. Cl.
CPC ............ *A61B 1/04* (2013.01); *A61B 1/00009* (2013.01); *G06K 9/4604* (2013.01); *G06T 7/13* (2017.01); *G06K 2209/05* (2013.01); *G06T 2207/10068* (2013.01)

(58) Field of Classification Search
CPC .................................................. G06K 9/4604
See application file for complete search history.

(56) References Cited

U.S. PATENT DOCUMENTS

| | | | |
|---|---|---|---|
| 6,778,690 B1* | 8/2004 | Ladak ............. | G06T 7/0012 382/131 |
| 7,011,625 B1* | 3/2006 | Shar ............... | G06T 7/602 382/128 |
| 2007/0025598 A1* | 2/2007 | Kobayashi ....... | G06K 9/522 382/117 |
| 2010/0027890 A1* | 2/2010 | Yoshinaga ....... | G06K 9/0061 382/195 |
| 2010/0298641 A1* | 11/2010 | Tanaka ............ | A61B 1/00147 600/109 |
| 2011/0164064 A1* | 7/2011 | Tanaka ............ | A61B 5/1075 345/667 |
| 2012/0140989 A1* | 6/2012 | Hori ................ | G06T 7/602 382/106 |
| 2012/0155724 A1* | 6/2012 | Kitamura ........ | G06T 7/0083 382/128 |

(Continued)

FOREIGN PATENT DOCUMENTS

JP    2013-207682 A    10/2013

*Primary Examiner* — Oneal R Mistry
(74) *Attorney, Agent, or Firm* — Oblon, McClelland, Maier & Neustadt, L.L.P.

(57) ABSTRACT

There is provided an image processing device including an edge detection unit configured to detect a boundary point between a first region including a subject to be observed and a second region that does not include the subject, a first estimation unit configured to estimate a first shape as a shape of a boundary between the first region and the second region based on the boundary point, and a second estimation unit configured to estimate a second shape as a shape of a boundary between the first region and the second region based on the boundary point and the estimated first shape.

8 Claims, 11 Drawing Sheets

(56) References Cited

U.S. PATENT DOCUMENTS

| | | | |
|---|---|---|---|
| 2013/0258080 A1* | 10/2013 | Kuriyama | A61B 1/00009 348/65 |
| 2014/0072230 A1* | 3/2014 | Ruan | G06T 7/12 382/199 |
| 2015/0294463 A1* | 10/2015 | Takahashi | G02B 23/2423 348/71 |

* cited by examiner

IMAGE PROCESSING DEVICE, IMAGE PROCESSING METHOD, AND PROGRAM

CROSS REFERENCE TO RELATED APPLICATIONS

This application claims the benefit of Japanese Priority Patent Application JP 2014-032808 filed Feb. 24, 2014, the entire contents of which are incorporated herein by reference.

BACKGROUND

The present technology relates to an image processing device, an image processing method, and a program. More particularly, the present technology relates to an image processing device, an image processing method, and a program, which are capable of accurately correcting a mask of an endoscope.

An endoscope is used as a medical instrument that is inserted into the body of a subject such as patients and observes the inside of the body. An image from an endoscope is displayed in the form of a circular frame on a rectangular screen. In such cases, it is necessary to detect an image portion in distinction from a lens barrel portion that is displayed as a portion shaded by a lens barrel.

A mask may be used to distinguish a portion that provides an image obtained by an endoscope for the user from a portion that does not provide an image for the user (refer to JP 2013-207682A).

SUMMARY

The position of a mask of an endoscope may be shifted frequently, and thus for example, if the position is shifted, it is desirable to detect and correct a mask.

The present technology is made in view of such circumstances, and it is intended that the detection of a mask is allowed to be performed with accuracy.

According to an embodiment of the present disclosure, there is provided an image processing device including an edge detection unit configured to detect a boundary point between a first region including a subject to be observed and a second region that does not include the subject, a first estimation unit configured to estimate a first shape as a shape of a boundary between the first region and the second region based on the boundary point, and a second estimation unit configured to estimate a second shape as a shape of a boundary between the first region and the second region based on the boundary point and the estimated first shape.

The subject to be observed may be a living body captured by an endoscopic device.

The first estimation unit may estimate the first shape to be circular, and the second estimation unit may estimate the second shape to be elliptical.

The image processing device may further includes an edge deletion unit configured to delete the boundary point located within the first shape from among the boundary points.

The edge detection unit may detect the boundary point based on a luminance value of a pixel.

The edge detection unit may detect the boundary point using two rectangular filters arranged to be spaced by a predetermined number of pixels.

The edge detection unit may detect the boundary point based on standard deviation of the luminance value.

The standard deviation may be calculated from a relational expression between the luminance value and the standard deviation, the relational expression being determined in advance.

The edge detection unit may be included in a first operation unit, the first estimation unit and the second estimation unit may be included in a second operation unit, and one of the first operation unit and the second operation unit may be configured to include a central processing unit (CPU), and the other may be configured to include a graphics processing unit (GPU).

According to another embodiment of the present disclosure, there is provided an image processing device including an edge detection unit configured to detect a boundary point between a first region including a subject to be observed and a second region that does not include the subject, a first estimation unit configured to set a weight for the boundary point based on a predetermined reference shape, and a second estimation unit configured to estimate a shape of a boundary between the first region and the second region based on the boundary point to which the weight is set.

The subject to be observed may be a living body captured by an endoscopic device.

The predetermined reference shape may be circular.

The predetermined reference shape may be set based on information of the endoscopic device.

The second estimation unit may estimate the shape of the boundary between the first region and the second region to be elliptical.

A first image processing method according to an embodiment of the present disclosure includes detecting a boundary point between a first region including a subject to be observed and a second region that does not include the subject, estimating a first shape as a shape of a boundary between the first region and the second region based on the detected boundary point, and estimating a second shape as a shape of a boundary between the first region and the second region based on the estimated first shape and the boundary point.

A second image processing method according to an embodiment of the present disclosure includes detecting a boundary point between a first region including a subject to be observed and a second region that does not include the subject, setting a weight for the detected boundary point based on a predetermined reference shape, and estimating a shape of a boundary between the first region and the second region based on the boundary point to which the weight is set.

According to another embodiment of the present disclosure, there is provided a program for causing a computer to execute detecting a boundary point of a boundary between a first region including a subject to be observed and a second region that does not include the subject, estimating a first shape as a shape of a boundary between the first region and the second region based on the detected boundary point, and estimating a second shape as a shape of a boundary between the first region and the second region based on the estimated first shape and the boundary point.

In the first image processing device, the first image processing method, and the program therefor according to an embodiment of the present technology, a boundary point between a first region including a subject to be observed and a second region that does not include the subject is detected, a first shape is estimated as a shape of a boundary between the first region and the second region based on the detected boundary point, and a second shape is estimated as a shape of a boundary between the first region and the second region based on the estimated first shape and the boundary point.

In the second image processing device, the second image processing method, and the program therefor according to an embodiment of the present technology, a boundary point between a first region including a subject to be observed and a second region that does not include the subject is detected, weight is set for the detected boundary point based on a predetermined reference shape, and a shape of a boundary between the first region and the second region is estimated based on the boundary point to which the weight is set.

In the image processing device, the second image processing method, and the program therefor according to an embodiment of the present technology, a boundary point of a boundary between a first region that provides a captured image for a user and a second region that does not provide it is detected, a first shape is estimated from the detected boundary point, and a second shape is estimated from the detected boundary point. A shape of boundary between the first region and the second region is detected by two stages of estimation that includes estimation of the first shape and estimation of the second shape.

According to an embodiment of the present technology, the detection of a mask is allowed to be performed with accuracy.

Note that the advantages herein are not necessarily intended to be restrictive, and any other advantage described in the present disclosure may be achievable.

DETAILED DESCRIPTION OF THE EMBODIMENT(S)

Embodiments for implementing the present technology (hereinafter simply referred to as "embodiment") will be described. The description will be made in the following order.

1. Configuration of image processing device according to first embodiment

2. Operation by image processing device according to first embodiment

3. Configuration of image processing device according to second embodiment

4. Operation by image processing device according to second embodiment

5. Recording medium

<Configuration of Image Processing Device According to First Embodiment>

An image processing device described herein is an image processing device for processing an image obtained from, for example, an endoscope. The present technology described herein may be applied to any device for acquiring an image and detecting a mask from the acquired image other than the device for processing an image obtained from an endoscope. The following description will be made by taking, as an example, an image processing device for processing an image obtained from an endoscope.

Figure 1:
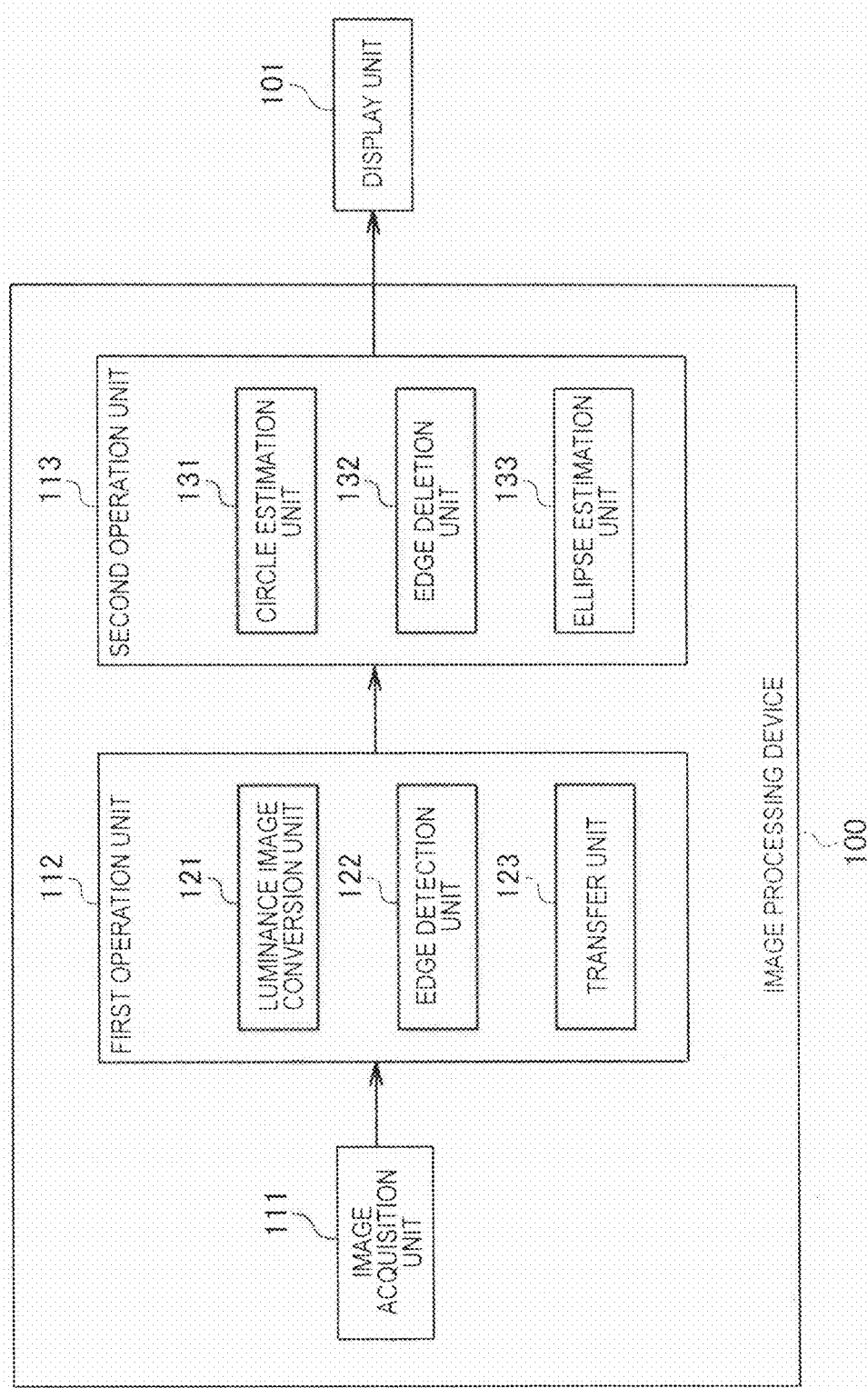
FIG. 1 is a diagram illustrating the configuration of an embodiment of an image processing device to which the present technology is applied.

FIG. 1 is a diagram illustrated to describe the configuration of an image processing device according to a first embodiment. The image processing device 100 shown in FIG. 1 acquires image data from an endoscopic device (not shown) used as medical instruments, processes the acquired image, and outputs the processed image to a display unit 101 such as a monitor for displaying the image.

The image processing device 100 is configured to include an image acquisition unit 111, a first operation unit 112, and a second operation unit 113. The first operation unit 112 is configured to include a luminance image conversion unit 121, an edge detection unit 122, and a transfer unit 123. The second operation unit 113 is configured to include a circle estimation unit 131, an edge deletion unit 132, and an ellipse estimation unit 133.

The image acquisition unit 111 of the image processing device 100 acquires an image from an endoscopic device (not shown). The endoscopic device is configured to include an endoscope, a light source unit, an imaging means, and a camera control unit. The endoscope forms an in-vivo imaging device inserted into the body cavity for capturing the inside of the body. The light source unit supplies illumination light to the endoscope. The imaging means of the endoscope may be a charge-coupled device (CCD). The camera control unit performs signal processing for the imaging means. The image acquisition unit 111 acquires image data outputted from the camera control unit.

The image data acquired by the image acquisition unit 111 is supplied to the first operation unit 112. The luminance image conversion unit 121 included in the first operation unit 112 converts the acquired image data into image data of a luminance image and supplies the converted image data to the edge detection unit 122.

Figure 2:
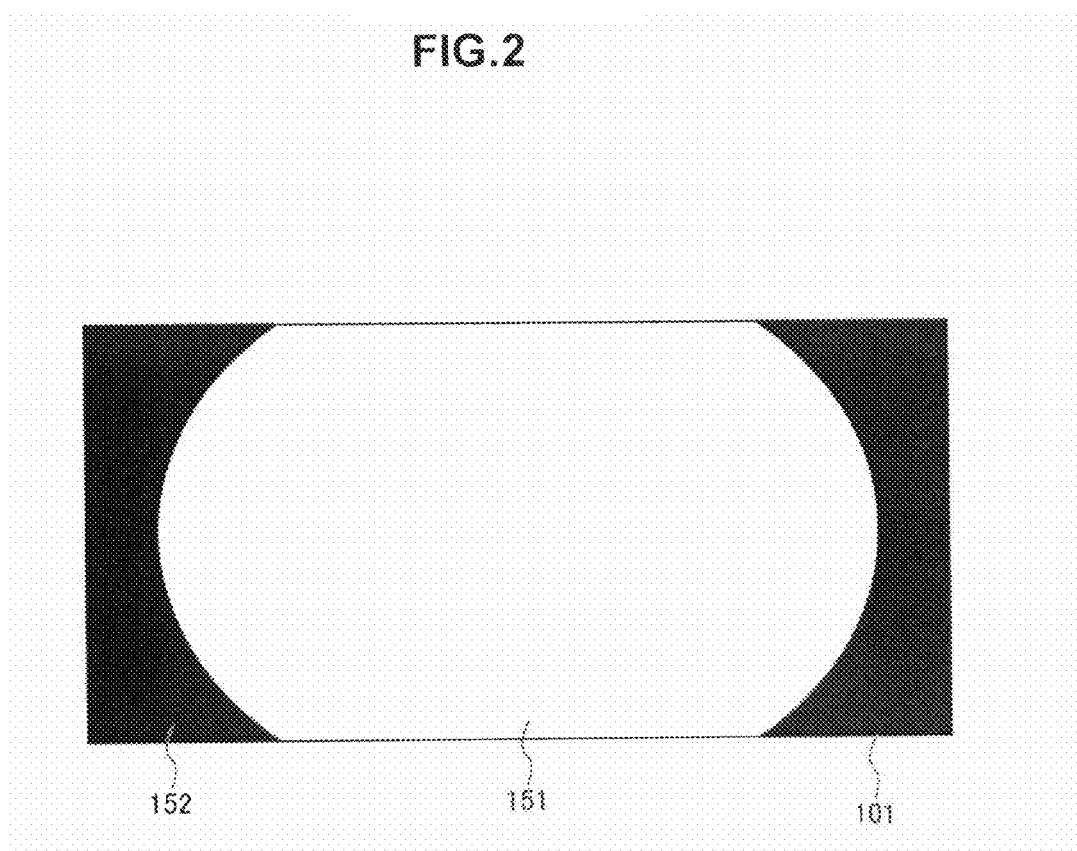
FIG. 2 is a diagram illustrated to describe a mask.

The edge detection unit 122 detects an edge portion using the luminance image based on the supplied image data. Referring to FIG. 2, an edge (mask shape) is described. FIG. 2 illustrates an exemplary image displayed on the display unit 101. The center portion in the screen is an elliptical effective region 151, which presents an image captured by the endoscopic device to the user.

The periphery of the effective region 151 in the image is a mask region 152, which is, for example, a blackened region as shown in FIG. 2. The boundary between the effective region 151 and the mask region 152 in the image is an edge. The edge detection unit 122 detects such a boundary. In the present technology, as described later, the edge detection unit 122 detects an edge and then the detected edge is corrected, thereby obtaining an accurate edge (detection of a mask).

There is a region in which an in-vivo image is invisible at left, right, upper and lower parts of the image obtained by the endoscope. This is because there is a region in which light is not transmitted to the imaging means due to the existence of vignetting in the endoscope. The region in which an in-vivo image is invisible corresponds to the mask region 152, and the region in which an in-vivo image is visible corresponds to the effective region 151.

The occurrence condition of vignetting is likely to be changed because the endoscope is shifted. If the occurrence condition of vignetting is changed, the mask region 152 is also likely to be changed. Thus, it is necessary to check a change in the mask region 152 and to appropriately deal with the change. In other words, it is necessary to accurately detect a mask, and in the present technology described later, the edge detection unit 122 detects an edge and then the detected edge is corrected, thereby obtaining an accurate edge (detection of a mask).

Referring back to the description of the image processing device 100 shown in FIG. 1, the transfer unit 123 transfers information regarding an edge detected by the edge detection unit 122 to the second operation unit 113.

The circle estimation unit 131 included in the second operation unit 113 estimates the shape of a mask (shape of an edge) to be circular. When an edge detected by the edge detection unit 122 is within the circle estimated by the circle estimation unit 131, the edge deletion unit 132 deletes the edge.

The ellipse estimation unit 133 detects a mask by estimating the shape of a mask to be elliptical using information regarding the remaining edge that is not deleted by the edge deletion unit 132.

In this way, in the present technology, estimation is performed twice by the circle estimation unit 131 and the ellipse estimation unit 133 included in the second operation unit 113, thereby detecting a mask. The estimation result obtained by the ellipse estimation unit 133 is outputted, as a shape of the detected mask, to the display unit 101 disposed in the stage following the ellipse estimation unit 133.

The following description will be given by taking an embodiment in which circle estimation is performed and then ellipse estimation is performed as an example, but the application scope of the present technology is not limited to the order of estimation as described above.

As shown in FIG. 2, when the mask region 152 (or effective region 151) displayed on the display unit 101 is elliptical, the circle estimation is performed and then the ellipse estimation is performed. Alternatively, in this case, it is also possible to perform the ellipse estimation and then the ellipse estimation.

Furthermore, when the mask region 152 (or effective region 151) displayed on the display unit 101 is circular (not shown), the circle estimation is performed and then the circle estimation may be performed. Alternatively, in this case, it is also possible to perform the ellipse estimation and then the circle estimation.

In the image processing device 100 shown in FIG. 1, the first and second operation units 112 and 113 may be configured to include a central processing unit (CPU) or a graphics processing unit (GPU). The first and second operation units 112 and 113 may be configured as separate operation units or as a single component, included in the image processing device 100.

The first and second operation units 112 and 113 may be mounted in the same image processing device 100. Alternatively, the first and second operation units 112 and 113 may be mounted in the individual corresponding devices and may transfer edge information through a cable that is respectively connected to them.

Specifically, for example, the first operation unit 112 may be configured to include a GPU to convert an image obtained from an endoscopic device into luminance data and detect an edge. The second operation unit 113 may be configured to include a CPU to detect a mask using an edge detected by the GPU.

<Operation by Image Processing Device According to First Embodiment>

Figure 3:
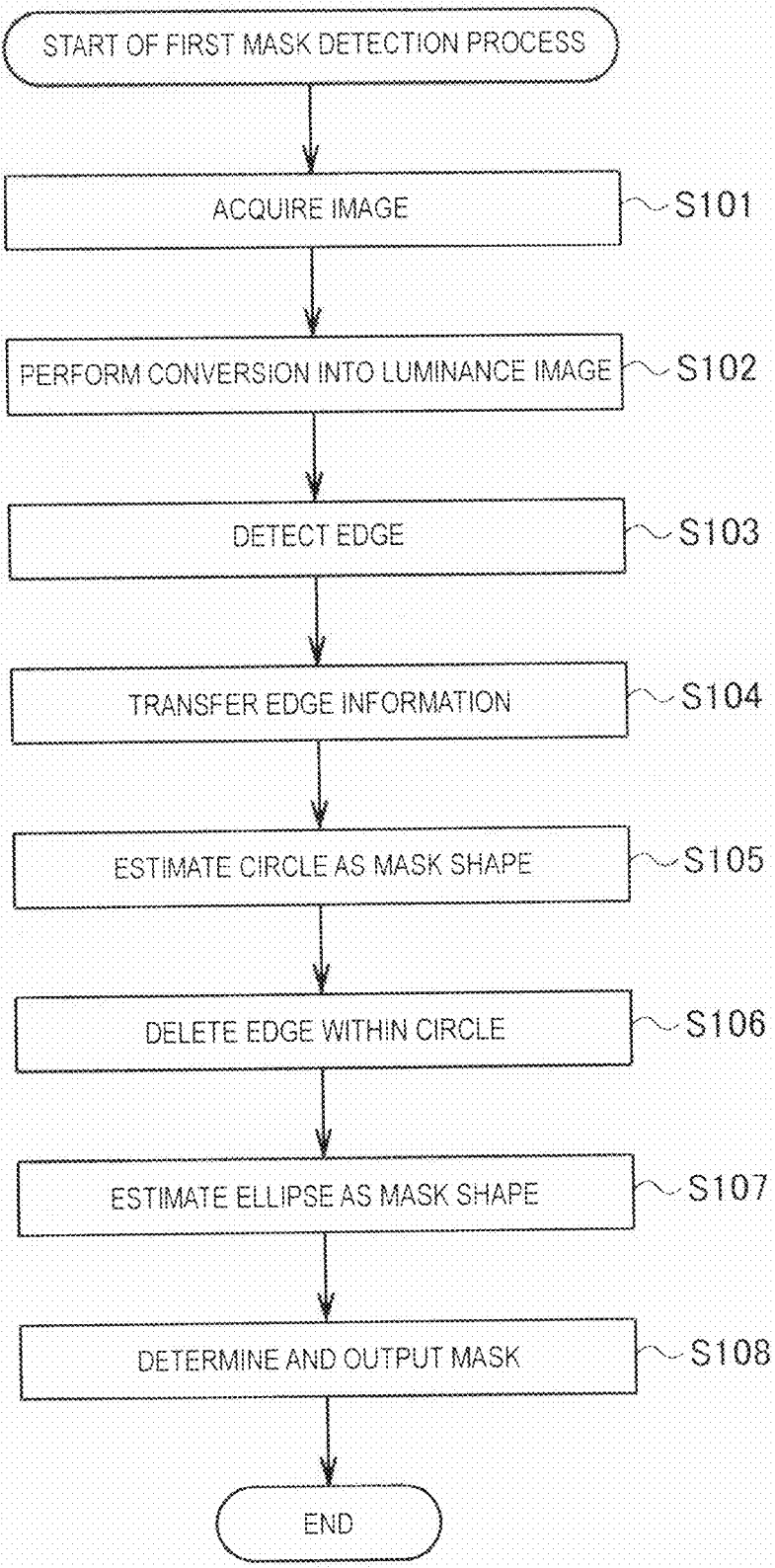
FIG. 3 is a flowchart illustrated to describe the operation performed by the image processing device.

Referring to the flowchart of FIG. 3, the operation performed by the image processing device 100 shown in FIG. 1 is described.

In step S101, the image acquisition unit 111 included in the image processing device 100 acquires image data from an endoscopic device (not shown).

In step S102, the luminance image conversion unit 121 included in the first operation unit 112 converts an image based on the image data acquired by the image acquisition unit 111 into luminance image, and supplies the converted image data to the edge detection unit 122.

The edge detection unit 122 detects an edge that is a boundary portion between the effective region 151 and the mask region 152 (see FIG. 2) from the luminance image, as described with reference to FIGS. 4 and 5.

The detection of an edge by the edge detection unit 122 is described with reference to FIGS. 4 and 5.

Figure 4:
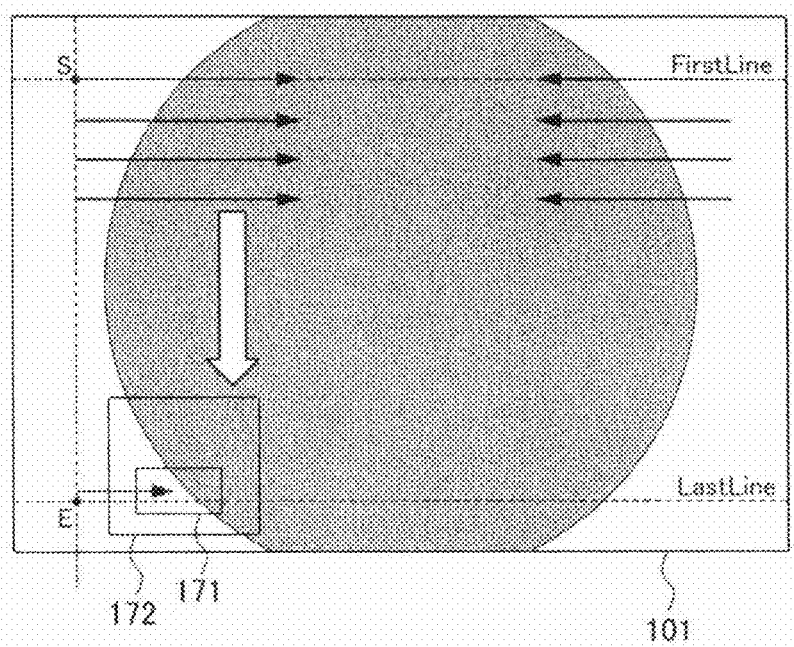
FIG. 4 is a diagram illustrated to describe the detection of an edge.

FIG. 4 illustrates an exemplary screen displayed on the display unit 101. An exemplary screen shown in FIG. 4 is substantially similar to an exemplary screen shown in FIG. 2, but for convenience of description, the mask region 152 is represented in white and the effective region 151 is represented in gray. The edge detection unit 122 scans a luminance image from the upper left to the right. On the other hand, the edge detection unit 122 also scans a luminance image from the upper right to the left.

In other words, the edge detection unit 122 scans a luminance image in the left and right directions. The scanning in the left and right directions is similarly performed to each other. Thus, the description will be given by taking the scanning in the left direction as an example.

The scanning may be started from a line that is uppermost, or may be started from a line located at a lower side by a predetermined number of lines from the uppermost line. The scanning may be started from a pixel located at the leftmost, or the scanning may be started from a pixel located at the right side by a predetermined number of pixels from the leftmost pixel. The description will be given on the assumption that the scanning is started from a pixel S shown in FIG. 4.

When the scanning is started from the pixel S in the right direction and the scanning for a predetermined number of pixels is completed, a portion to be scanned is shifted to the next line. Alternatively, when the scanning is started from the pixel S in the right direction and an edge is detected, a portion to be scanned is shifted to the next line.

In this way, when the scanning in a predetermined range for each line is performed, the scanning for the relevant line may be completed, or the scanning for the relevant line may be completed when an edge is detected. In other words, the range to be scanned may be set to be fixed or variable.

The scanning is completed at a line in which a pixel E is located. The pixel E is a pixel on a line located on the upper side by a predetermined number of lines from a line located at the bottom, and the pixel E is a pixel located at the same position as the pixel S from the left side.

At the time when the scanning is started from the pixel S and the scanning starting from the pixel E is completed, scanning related to the edge detection is completed. All the lines between a line in which the pixel S is located and a line in which the pixel E is located may be a target to be scanned. Alternatively, lines arranged to be spaced by a predetermined number of lines may be a target to be scanned.

The scanning is performed using a predetermined filter 171. FIG. 5 is a diagram illustrated to describe the filter 171 and is an enlarged diagram of a region 172 in the screen shown in FIG. 4. In FIG. 5, the mask region 152 is represented in black and the effective region 151 is represented in gray.

The filter 171 is composed of rectangular filters 181-1 and 181-2. In the following description, when there is no necessity for a distinction between the filter 181-1 and the filter 181-2, these units will be simply referred to as a filter 181. This is similarly applied to other components.

The filter 181 is a rectangular shape with the size in which the length of the long side in the horizontal direction is set to width W and the length of the short side in the vertical direction is set to height H. The number of pixels contained in the filter 181, that is, the size of width W by height H is set to 20 or more.

The filter 181-1 and the filter 181-2 are separated by a predetermined number of pixels contained between them. The spacing between the filter 181-1 and the filter 181-2 is referred to as a gap G.

In this way, in the filter 171 including the filters 181-1 and 181-2 which are separated by the gap G between them, the scanning is performed by shifting the filter 171 from the left to the right.

With the scanning, the average luminance value in the filter 181-1 and the average luminance value in the filter 181-2 are calculated separately, and an edge is detected based on the difference between the average luminance values. For example, when the filters 181-1 and 181-2 are in the mask region 152, it is considered that the average luminance values of the filters 181-1 and 181-2 are both low and the difference between the average luminance values of the filters 181-1 and 181-2 is also low.

On the other hand, when the filter 181-1 is in the mask region 152 and the filter 181-2 is in the effective region 151, it is considered that the average luminance value in the filter 181-1 is low, the average luminance value in the filter 181-2 is high (at least higher than the average luminance value in the filter 181-1), and the difference between the average luminance values in the filters 181-1 and 181-2 is large.

Figure 6:
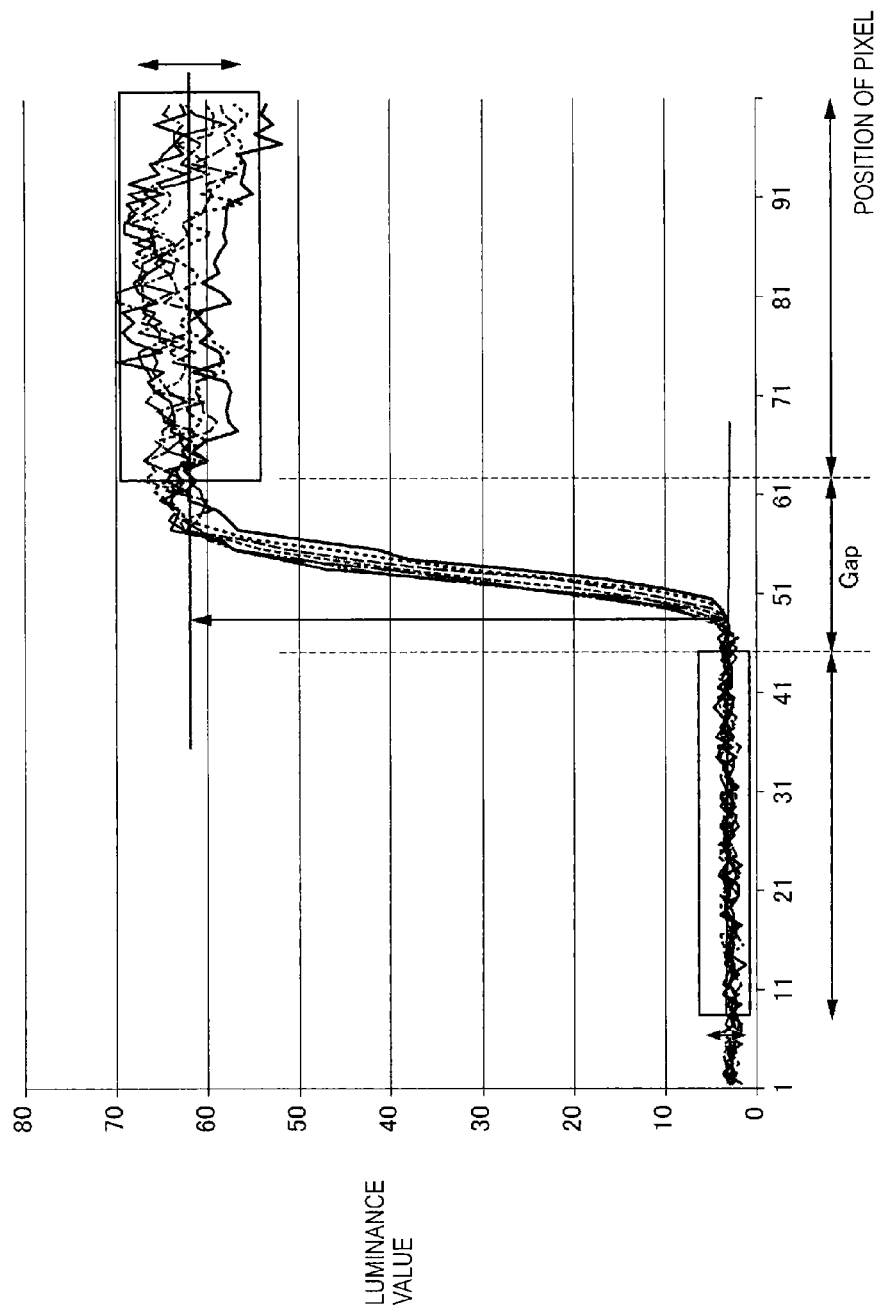
FIG. 6 is a diagram illustrated to describe the detection of an edge.

FIG. 6 illustrates an example of a luminance value when the filter 181-1 is in the mask region 152 and the filter 181-2 is in the effective region 151.

In the graph shown in FIG. 6, the horizontal axis represents the position of a pixel and the vertical axis represents a luminance value of a pixel. In addition, the graph shown in FIG. 6 indicates the result of measurement at seven parts in a portion in which an edge exists. A pixel located at a position preceding the position of a pixel 43 (hereinafter, referred to as "position 43") has a low luminance value that is smaller than or equal to 10. A pixel located at a position following the position of a pixel 62 (hereinafter, referred to as "position 62") has a high luminance value that is greater than or equal to 60. There is an edge in the position of pixels between the position 43 and the position 62, and the luminance value is changed at positions preceding and following the position including an edge.

When the filter 181-1 is in the mask region 152, it is located at a position preceding the position of pixel 43, and thus the average value of the luminance value in the filter 181-1 has a small value, in this case, 10 or less.

On the other hand, when the filter 181-2 is in the effective region 151, it is located at a position following the position of pixel 62, and thus the average value of the luminance value in the filter 181-2 has a large value, in this case, 60 or more.

In this way, a difference occurs between the average luminance values in the filter 181 depending on whether the filter 181 is located in the mask region 152. Detection of an edge is performed using this difference. In a case as shown in FIG. 6, when there is an edge in the position of pixels between the position 43 and the position 62 and the gap G of the filter 171 is located at that portion, an edge is detected.

Figure 5:
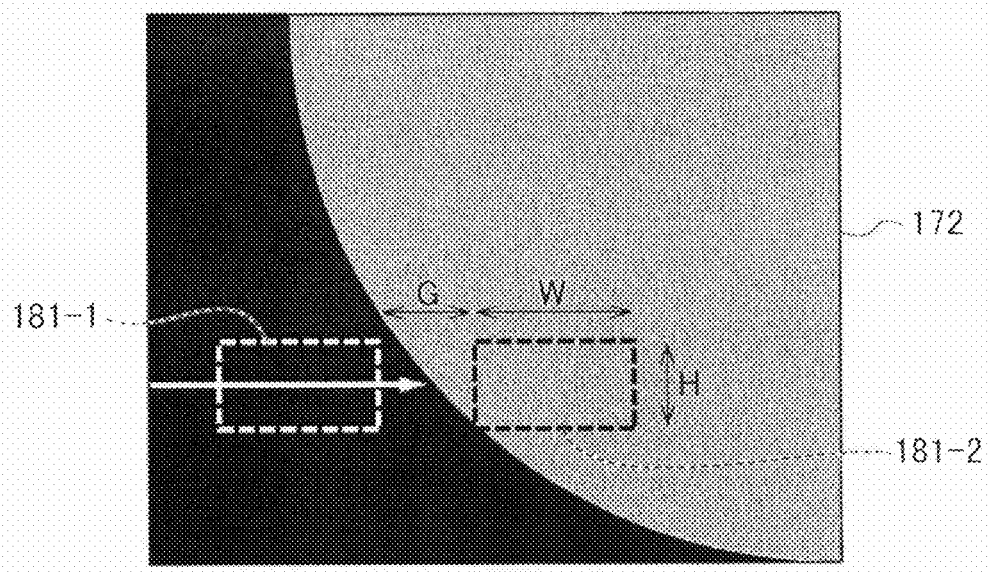
FIG. 5 is a diagram illustrated to describe the detection of an edge.

The filter 171 shown in FIG. 5 includes the filters 181-1 and 181-2 and the gap G is provided between the filters 181-1 and 181-2, and this corresponds to when the filter 181-1 is in the mask region 152 and the filter 181-2 is in the effective region 151. This is intended to detect when an edge exists within the gap G.

In this way, the average luminance values in the filters 181-1 and 181-2 are calculated separately, and when the difference between the average luminance values is greater than or equal to a predetermined value, it is detected that an edge exists within the gap G.

In this way, the position of an edge may be detected by detecting a position in which the difference between the average luminance values is greater than or equal to a predetermined value. Furthermore, the standard deviation is obtained, and the position of an edge may be detected using the obtained standard deviation.

The description will be given by taking a case in which a point with high dispersion is set as an edge of a mask as an example. The dispersion is a value obtained by dividing the difference between the average luminance values by the standard deviation.

Dispersion=(Difference between average luminance values)/Standard deviation

The point with high dispersion is set as an edge of a mask. Specifically, a threshold is set to approximately 1.5 times the standard deviation, and an edge may be allowed to be detected when the dispersion is greater than or equal to the threshold.

When the standard deviation is intended to be used, it is necessary to calculate the standard deviation from a luminance value actually measured, this increases the amount of calculation. Thus, if the real time property is emphasized, the dispersion may be calculated using the standard deviation previously calculated as described later rather than calculation of the standard deviation from the luminance value actually measured.

Figure 7:
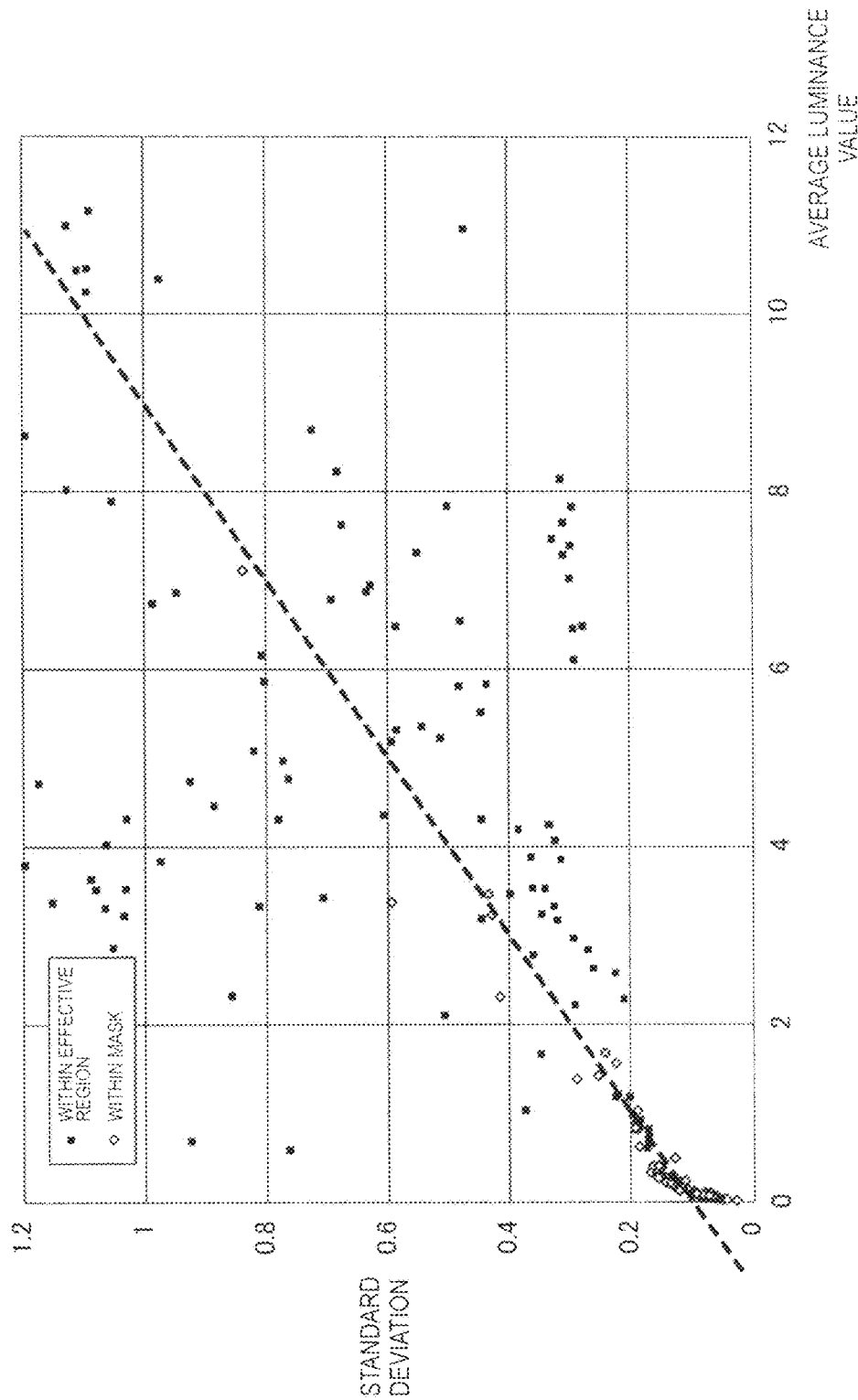
FIG. 7 is a diagram illustrated to describe the detection of an edge.

The graph shown in FIG. 7 indicates a relationship between the average luminance value and the standard deviation. In the graph, the horizontal axis represents the average luminance value, and the vertical axis represents the standard deviation. FIG. 7 illustrates a point obtained by plotting actually measured values. A square point is a point obtained by plotting a value obtained from a pixel located in the effective region 151. A diamond-shaped point is a point obtained by plotting a value obtained from the mask region 152.

A linear expression is determined using the least squares method and other like method from the distribution of these points, and thus a relational expression established between the average luminance value and the standard deviation is determined. The linear line represented by dotted lines in FIG. 7 is the relational expression determined as described above. The standard deviation at the time of determining the dispersion is determined from the relational expression shown in FIG. 7. For example, when the average luminance value is 6.0, a value of 0.7 is used as the standard deviation and the dispersion is calculated.

Such a relational expression is stored in the edge detection unit 122, and when the average luminance value is calculated, the standard deviation may be determined by substituting the average luminance into the stored relational expression. Alternatively, a table in which the average luminance value and the standard deviation are associated with each other is stored in the edge detection unit 122, and when the average luminance value is calculated, the standard deviation may be read by referring to the stored table.

Such a relational expression may be used in common for each image processing device 100, but it is preferable for the relational expression to be determined for each endoscopic device in consideration of individual differences or the like of endoscopic devices. For example, when an endoscopic device is connected to the image processing device 100, the endoscopic device captures a test pattern or the like and obtains an actual measurement value from an image upon capturing, thereby determining a relational expression.

When a relational expression is likely to be changed depending on use environment or other factors, a process for determining a relational expression may be performed as an initial setting at the time when processing by the image processing device 100 is started.

In this way, by setting the relationship between the average luminance value and the standard deviation in advance, it is possible to reduce the amount of calculation that is necessitated upon the detection of an edge, and real time processing is possible.

It is possible to reduce the number of edges obtained by an erroneous detection, as compared with the case in which the standard deviation is determined using a value obtained by actual measurement and then the dispersion is determined.

When the standard deviation is determined by actual measurement, in the graph of FIG. 7, it can be seen that the standard deviation fluctuates as shown by points. Thus, if the standard deviation is determined by actual measurement, an erroneous detection of an edge is likely to be increased due to the fluctuation in the standard deviation. However, as described above, by establishing the relationship between the average luminance value and the standard deviation in advance, the fluctuation in the standard deviation is absorbed and thus an erroneous detection of an edge can be reduced.

In this way, an edge is detected by performing the scanning using the filter 171 for the luminance image. The following description is given on the assumption that an edge detected on a predetermined line is indicated as an edge point and the edge is a collection of edge points. In addition, the edge point is a point detected from a single line, and the description is assumed to include coordinates of a point detected as an edge.

The edge point is a point located at the boundary between a region representing an image provided to the user (effective region 151 in FIG. 2) and a region that does not provide an image to the user (mask region 152 in FIG. 2) from among images obtained by the endoscopic device, and it may be a point that can be also referred to as a boundary point.

The edge points detected by the edge detection unit 122 (see FIG. 1) are gathered in a predetermined arrangement and are transferred to the second operation unit 113 through the transfer unit 123 (step S104 in FIG. 3).

In step S105, the circle estimation unit 131 estimates a circle as a mask shape. In an exemplary screen shown in FIG. 8, the mask shape is assumed to be a shape of the boundary between an effective region 151' and the mask region 152'. The exemplary screen shown in FIG. 8 illustrates that the mask is circular in shape.

The estimation of a circle is performed under the assumption that the mask shape is circular, and a circular shape is estimated from information regarding the edge detected by the edge detection unit 122. In other words, a parameter for specifying a circle is estimated from edge information. The parameter includes the center point (center coordinates) and radius of the circle.

Figure 8:
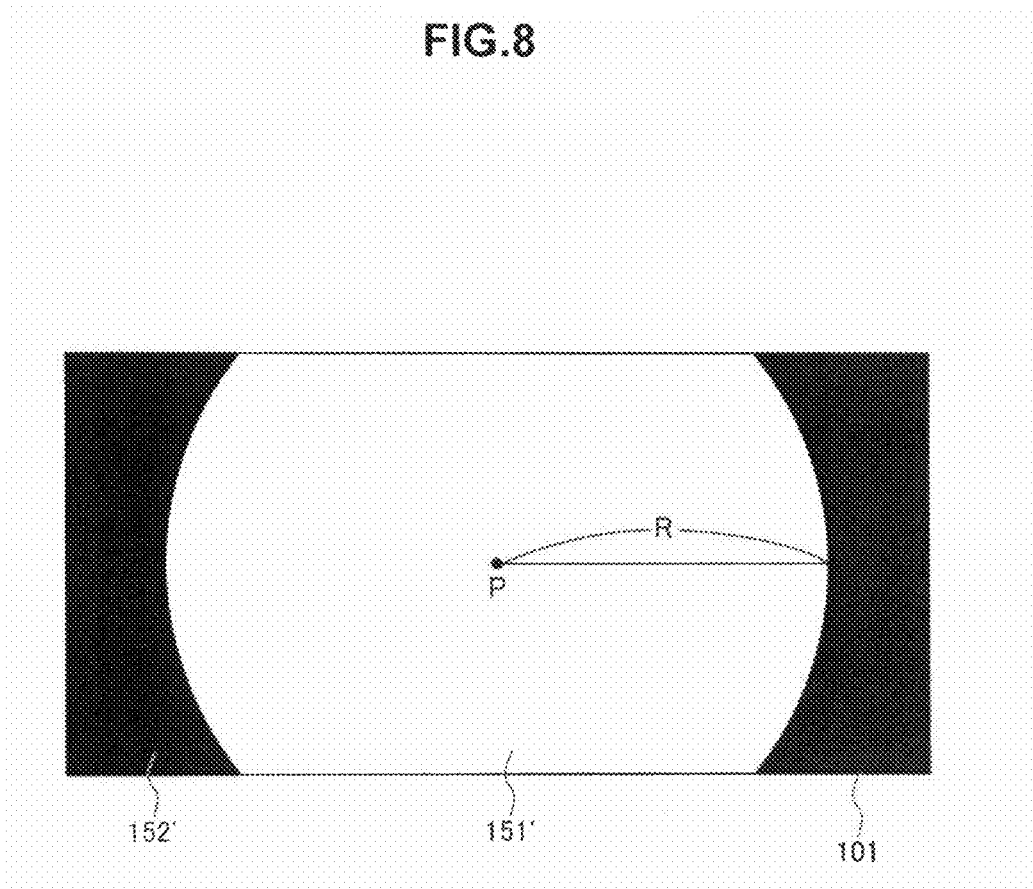
FIG. 8 is a diagram illustrated to describe an edge.

In the exemplary screen shown in FIG. 8, the center point is represented as point P, and the radius is represented as radius R. The circle estimation unit 131 calculates the coordinates of the point P and the radius R from the edge information. This estimation may be performed by the least squares method using the edge information (information regarding coordinates of an edge point).

In step S106, the edge deletion unit 132 deletes an edge point located within the circle estimated by the circle estimation unit 131 from among edge points detected by the edge detection unit 122.

If the edge information used at the time of performing an estimation by the circle estimation unit 131 is set as first edge information, the edge deletion unit 132 deletes information regarding the edge point located within the estimated circle from the first edge information and generates second edge information.

In step S107, the ellipse estimation unit 133 estimates an ellipse as a mask shape. The estimation of an ellipse is performed under the assumption that the mask shape is elliptical, and an elliptical shape is estimated from the second edge information generated by the edge deletion unit 132. In other words, a parameter for specifying an ellipse is estimated from the second edge information. The parameter includes the center point (center coordinates), length of long axis (major axis), and length of short axis (minor axis) of the ellipse.

As shown in FIG. 2, the mask shape is elliptical and thus the mask shape is estimated, for example, by the least squares method using the second edge information. The result obtained by the estimation is outputted to the display unit 101 as a mask shape (processing in step S108).

In this way, in the present embodiment, the mask shape is determined by performing the estimation twice. Two stages of estimation are performed by estimating the mask shape to be different in shape such as a circle and an ellipse. The mask shape is determined by performing two stages of estimation and thus it is possible to improve the detection accuracy of a mask shape.

This improvement is achieved by deleting an edge point that is more likely to be an erroneous detection by the first stage of estimation to leave an edge point that is more likely to be a correct detection and then the second stage of estimation is performed on the remaining edge point.

As described with reference to FIG. 4 or 5, the detection of an edge is performed using a rectangular filter or using the relationship between the average luminance value and the standard deviation, and thus the accuracy of the first edge information used in the first stage of estimation can be improved. Thus, the detection accuracy of the finally obtained mask shape can be improved.

The detection of a mask is often performed using the Hough transform in the past, but the Hough transform is characterized by lack of real-time property, and thus it is not suitable for image processing which necessitates the real-time property in an endoscopic device or other like devices.

Meanwhile, in the first embodiment described above, by employing the least squares method with relatively small amount of calculation, it is possible to reduce the amount of calculation, and thus the time for the mask detection can be shortened. In addition, the relationship between the average luminance value and the standard deviation is determined in advance upon a detection of an edge by the edge detection unit 122, and thus it is possible to achieve a further shortening of processing time by using the relationship.

Thus, according to an embodiment of the present technology, it is possible to detect a mask with higher accuracy, and the time for the mask detection can be shortened.

Although it has been described that the ellipse estimation unit 133 performs the ellipse estimation after the circle estimation unit 131 performs the circle estimation, the application of the present technology is not limited to a combination of the circle estimation and the ellipse estimation.

If a mask shape presented to the display unit 101 is elliptical, the second stage of estimation is the ellipse estimation, but if a mask shape presented to the display unit 101 is circular, it is preferable to perform the circle estimation. In addition, the present technology may be applied to any case in which the first stage of estimation is the circle estimation or the ellipse estimation.

Although the description is given by taking a circle or an ellipse as an example, the estimation using other shapes such as a rectangular shape may be performed in any one of the first stage of estimation and the second stage of estimation, or in the both stages.

Although it has been described that two stages of estimation are performed, three or more stages of estimation may be performed. However, if the number of times the estimation is performed increases, the number of times the operation is performed increases accordingly. In this case, the time for the mask detection is likely to be lengthened, and thus it is preferable that the number of times the estimation is performed is set to shorten the time for the mask detection and to improve the detection accuracy.

<Configuration of Image Processing Device According to Second Embodiment>

Figure 9:
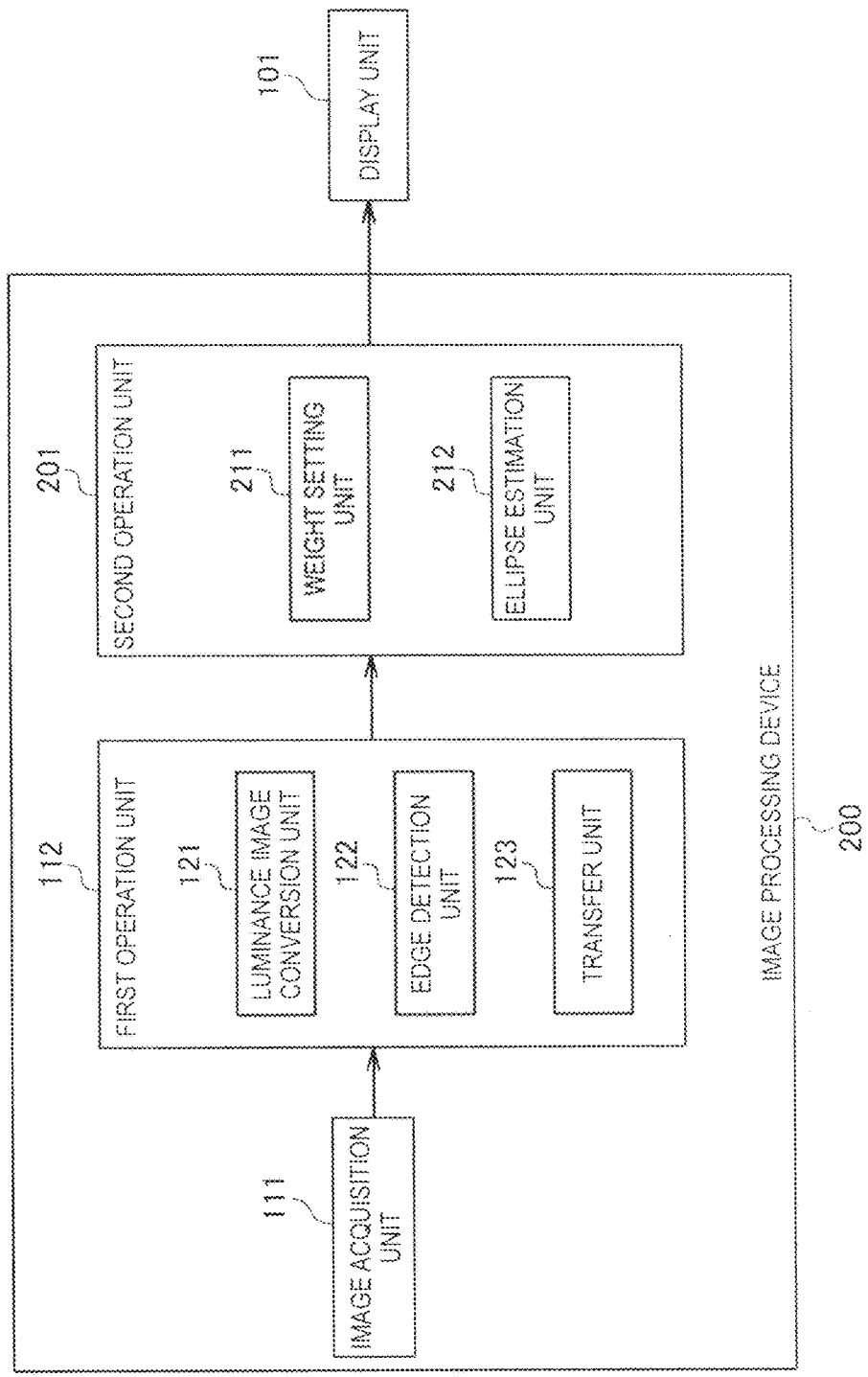
FIG. 9 is a diagram illustrating the configuration according to another embodiment of an image processing device to which the present technology is applied.

FIG. 9 illustrates the configuration of an image processing device according to a second embodiment. The image processing device 200 shown in FIG. 9 acquires image data from an endoscopic device (not shown) used as medical instruments, processes the acquired image, and outputs the processed image to a display unit 101 such as a monitor, which is similar to the image processing device 100 according to the first embodiment shown in FIG. 1.

In the image processing device 200 shown in FIG. 9 and the image processing device 100 shown in FIG. 1, the same components are denoted by the same reference numerals, and description thereof will be omitted as appropriate.

The image processing device 200 is configured to include an image acquisition unit 111, a first operation unit 112, and a second operation unit 201. The first operation unit 112 is configured to include a luminance image conversion unit 121, an edge detection unit 122, and a transfer unit 123. The second operation unit 201 is configured to include a weight setting unit 211, and an ellipse estimation unit 212.

The image processing device 200 shown in FIG. 9 is different from the image processing device 100 shown in FIG. 1 in that the configuration of the second operation unit 201 is different between them. The image processing device 200 is provided with the weight setting unit 211, instead of the circle estimation unit 131 and the edge deletion unit 132 that are included in the image processing device 100 (FIG. 1)

<Operation by Image Processing Device According to Second Embodiment>

Figure 10:
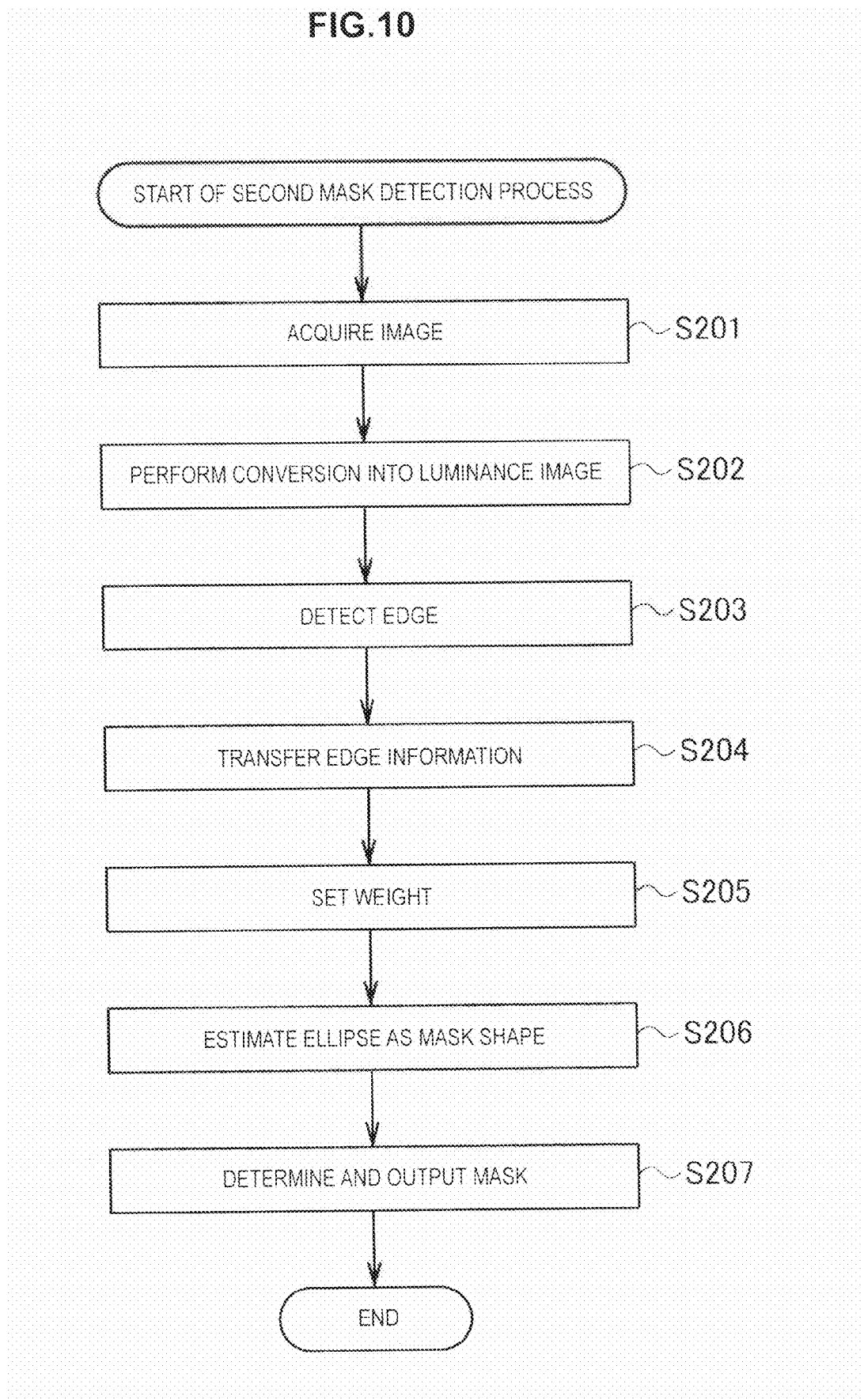
FIG. 10 is a flowchart illustrated to describe the operation performed by the image processing device.

Referring to the flowchart of FIG. 10, the operation performed by the image processing device 200 shown in FIG. 9 is described.

Processing of steps from S201 to S204 is similar to that of steps from S101 to S104 of the flowchart shown in FIG. 3, thus description thereof will be omitted. In other words, the processing performed by the image acquisition unit 111 of the image processing device 200 is similar to the processing performed by the image acquisition unit 111 (FIG. 1) of the image processing device 100. The processing performed by the first operation unit 112 of the image processing device 200 is similar to the processing performed by the first operation unit 112 (FIG. 1) of the image processing device 100

Thus, in the second embodiment, advantages of shortening the time for edge detection are achievable, which is similar to the first embodiment.

In step S205, a weight is set by the weight setting unit 211. In the weight setting unit 211, for example, a process of weighting as shown in FIG. 11 is performed on the edge information.

Figure 11:
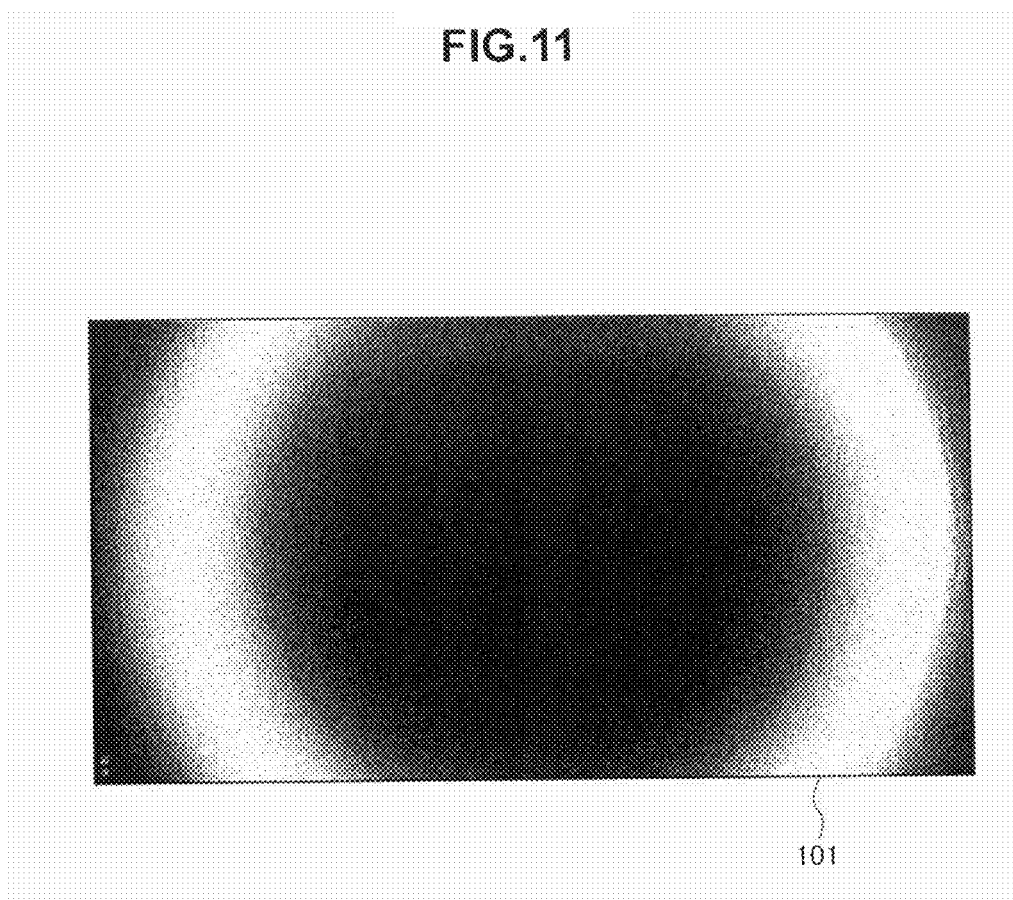
FIG. 11 is a diagram illustrated to describe weighting.

FIG. 11 is a diagram illustrated to describe a weighting performed by the weight setting unit 211 and illustrates an exemplary screen when a weight to be set is displayed on the display unit 101. The following description will be given on the assumption that a weighting value is set to one in a region in which an edge is more likely to exist, and a weighting value is set to zero in a region in which an edge is less likely to exist.

In FIG. 11, a portion represented in black is a region in which an edge is less likely to exist and a weighting value is set to zero. A portion represented in white is a region in which an edge is more likely to exist and a weighting value is set to one. In FIG. 11, the gradation is applied from the black region to the white region In other words, the weighting value is set to a numerical value between zero and one. The weighting value is set so that it gradually changes from a region set to zero to a region set to one. The following description will be given on the assumption that a weighting value is set, but a weighting value and a way to set the weighting value are not limited to examples described herein.

The weight setting unit 211 stores a reference shape used to perform a weighting as described above and performs a weighting based on the stored reference shape (pattern). Such a reference shape is preferable to be defined for each type of endoscope. In the endoscope, for example, because there are different series of systems, a reference shape is prepared for each system of endoscope, and information regarding the endoscope such as ID is obtained. Then, a weighting process may be performed by using a reference image associated with the ID.

As shown in FIG. 11, an edge is less likely to exist in a central portion or four corner portions of a screen, and thus a weighting value is set to zero. In this case, even if an edge point is detected at such portions, the weighting value is set to zero, thus such an edge point is not used for operation by the ellipse estimation unit 212 located at the subsequent stage.

The process of deleting an edge point detected from a predetermined region corresponds to the process of estimating a circle by the circle estimation unit 131 and of deleting an edge point within the circle by the edge deletion unit 132, in the first embodiment.

The image processing device 100 according to the first embodiment detects a mask by allowing the circle estimation unit 131 and the ellipse estimation unit 133 to perform two stages of estimation. The image processing device 200 according to the second embodiment performs a weighting process on the edge information as a process corresponding to the first stage of estimation.

This corresponds to the process of estimating a region in which an edge is more likely to exist when a mask shape is circular. In addition, this corresponds to the process of estimating a region in which an edge is less likely to exist and deleting an edge point within the region. In this way, such processing is performed in the second embodiment, and thus the process performed by the weight setting unit 211 corresponds to the process performed by the circle estimation unit 131 and the edge deletion unit 132 in the first embodiment, that is, this process corresponds to the first stage of estimation.

Even in the second embodiment, the ellipse estimation is performed as a process to be performed after step S205, and thus a mask is detected by performing two stages of estimation, which is similar to the first embodiment.

In this way, the edge information subjected to the weighting process by the weight setting unit 211 is supplied to the ellipse estimation unit 212. The edge information supplied to the ellipse estimation unit 212 is information that is obtained by excluding information that is less likely to be an edge, and if the information is more likely to be an edge, accordingly it significantly affects the estimation performed by the ellipse estimation unit 212.

In step S206, the ellipse estimation unit 212 detects a mask shape as an ellipse. Processing in step S206 may be performed in a similar way as the processing in step S107 (FIG. 3) performed by the ellipse estimation unit 133 of the image processing device 100, thus description thereof will be omitted. Processing in step S207 may be performed in a similar way as the processing in step S108 (FIG. 3), thus description thereof will be omitted.

In this way, according to the second embodiment, the weighting is performed so that a point, which is more likely to be an edge from among the detected edge points, affects the mask detection, and thus the accuracy of mask detection can be improved, thereby reducing the amount of calculation.

In the second embodiment, similarly to the first embodiment, it is possible to detect a mask with higher accuracy, thereby shortening the time for mask detection.

The embodiments of the present technology are capable of accurately detecting a mask when the exposure of an image captured by an endoscope is appropriate, or even excessive. When the exposure is appropriate or excessive, the contrast is noticeable between an image in the effective region 151 and an image in the mask region 152, and thus it is relatively easy to detect an edge located at the boundary between images and to detect a mask.

Moreover, the embodiments of the present technology are capable of accurately detecting a mask even when the exposure of an image captured by an endoscope is insufficient for the detection. When the exposure is insufficient for the detection, the contrast may be unnoticeable between an image in the effective region 151 and an image in the mask region 152. Even in such cases, it is possible to accurately detect a mask by detecting an edge and performing two stages of estimation, as described above.

<Recording Medium>

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

Figure 12:
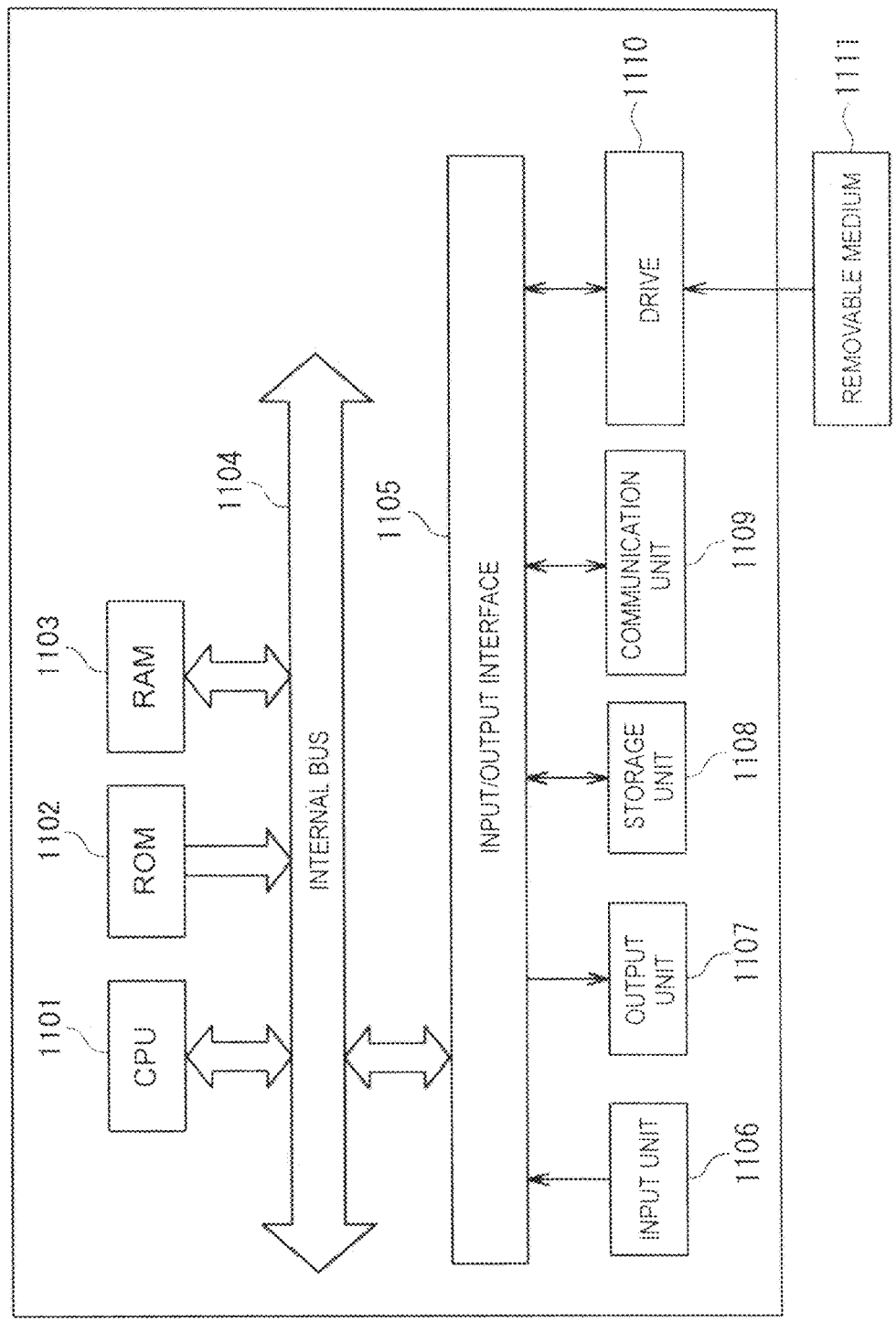
FIG. 12 is a diagram illustrated to describe a recording medium.

FIG. 12 is a block diagram illustrating a hardware configuration example of a computer for causing the above-described series of processes to be executed using a program. In the computer, a central processing unit (CPU) 1101, a read only memory (ROM) 1102, and a random access memory (RAM) 1103 are interconnected via a bus 1104. The bus 1104 is connected to an input/output interface 1105. The input/output interface 1105 is connected to an input unit 1106, an output unit 1107, a storage unit 1108, a communication unit 1109, and a drive 1110.

The input unit 1106 includes a keyboard, a mouse, a microphone, and other like devices. The output unit 1107 includes a display, a speaker, and other like devices. The storage unit 1108 includes a hard disk, a non-volatile memory, and other like devices. The communication unit 1109 includes a network interface and other like devices. The drive 1110 drives a removable medium 1111 such as a magnetic disk, an optical disk, a magneto-optical disk, a semiconductor memory or the like.

In the computer configured as described above, as one example the CPU 1101 loads a program stored in the storage unit 1108 via the input/output interface 1105 and the bus 1104 into the RAM 1103 and executes the program to carry out the series of processes described earlier.

Programs to be executed by the computer (CPU 1101) are provided being recorded in the removable medium 1111 in the form of a packaged medium or the like. The programs may be provided via a wired or wireless transmission medium, such as a local area network, the Internet, or digital satellite broadcasting.

In the computer, by inserting the removable medium 1111 into the drive 1110, the program can be installed in the storage unit 1108 via the input/output interface 1105. Further, the communication unit 1109 can receive the program via a wired or wireless transmission medium and can install it in the storage unit 1108. Moreover, the program can be installed in advance in the ROM 1102 or the storage unit 1108.

It should be noted that the program executed by a computer may be a program that is processed in time series according to the sequence described herein or a program that is processed in parallel or at necessary timing such as upon calling.

Note that the term "system" used herein refers to an entire configuration composed of a plurality of devices.

Note that the advantages described herein are to be considered illustrative or exemplary rather than restrictive, and other advantages that will be understood from the present technology may be achievable.

An embodiment of the technology is not limited to the embodiments described above, and various changes and modifications may be made without departing from the scope of the technology.

Additionally, the present technology may also be configured as below.

(1) An image processing device including:
an edge detection unit configured to detect a boundary point between a first region including a subject to be observed and a second region that does not include the subject;
a first estimation unit configured to estimate a first shape as a shape of a boundary between the first region and the second region based on the boundary point; and
a second estimation unit configured to estimate a second shape as a shape of a boundary between the first region and the second region based on the boundary point and the estimated first shape.

(2) The image processing device according to (1),
wherein the subject to be observed is a living body captured by an endoscopic device.

(3) The image processing device according to (1) or (2),
wherein the first estimation unit estimates the first shape to be circular, and
wherein the second estimation unit estimates the second shape to be elliptical.

(4) The image processing device according to any one of (1) to (3), further including:
an edge deletion unit configured to delete the boundary point located within the first shape from among the boundary points.

(5) The image processing device according to any one of (1) to (4),
wherein the edge detection unit detects the boundary point based on a luminance value of a pixel.

(6) The image processing device according to (5),
wherein the edge detection unit detects the boundary point using two rectangular filters arranged to be spaced by a predetermined number of pixels.

(7) The image processing device according to (5),
wherein the edge detection unit detects the boundary point based on standard deviation of the luminance value.

(8) The image processing device according to (7),
wherein the standard deviation is calculated from a relational expression between the luminance value and the standard deviation, the relational expression being determined in advance.

(9) The image processing device according to any one of (1) to (8),
wherein the edge detection unit is included in a first operation unit,
wherein the first estimation unit and the second estimation unit are included in a second operation unit, and
wherein one of the first operation unit and the second operation unit is configured to include a central processing unit (CPU), and the other is configured to include a graphics processing unit (GPU).

(10) An image processing device including:
an edge detection unit configured to detect a boundary point between a first region including a subject to be observed and a second region that does not include the subject;
a first estimation unit configured to set a weight for the boundary point based on a predetermined reference shape; and
a second estimation unit configured to estimate a shape of a boundary between the first region and the second region based on the boundary point to which the weight is set.

(11) The image processing device according to (10),
wherein the subject to be observed is a living body captured by an endoscopic device.

(12) The image processing device according to (10) or (11),
wherein the predetermined reference shape is circular.

(13) The image processing device according to (11) or (12),
wherein the predetermined reference shape is set based on information of the endoscopic device.

(14) The image processing device according to any one of (10) to (13),
wherein the second estimation unit estimates the shape of the boundary between the first region and the second region to be elliptical.

(15) An image processing method including:
detecting a boundary point between a first region including a subject to be observed and a second region that does not include the subject;
estimating a first shape as a shape of a boundary between the first region and the second region based on the detected boundary point; and
estimating a second shape as a shape of a boundary between the first region and the second region based on the estimated first shape and the boundary point.

(16) An image processing method including:
detecting a boundary point between a first region including a subject to be observed and a second region that does not include the subject;
setting a weight for the detected boundary point based on a predetermined reference shape; and
estimating a shape of a boundary between the first region and the second region based on the boundary point to which the weight is set.

(17) A program for causing a computer to execute:
detecting a boundary point of a boundary between a first region including a subject to be observed and a second region that does not include the subject;
estimating a first shape as a shape of a boundary between the first region and the second region based on the detected boundary point; and
estimating a second shape as a shape of a boundary between the first region and the second region based on the estimated first shape and the boundary point.

What is claimed is:

1. An image processing device comprising:
circuitry configured to:
acquire an image from an image sensor;
detect a plurality of boundary points between a first region including a subject to be observed and a second region that does not include the subject in the image;
estimate a shape of a boundary between the first region and the second region based on the plurality of boundary points as a first shape;
delete boundary points of the plurality of boundary points that fall within the first shape;
estimate the shape of the same boundary between the same first region and the same second region based on remaining boundary points of the plurality of boundary points as a second shape; and
display a mask shape based upon the second shape, wherein
the subject to be observed is a living body captured by an endoscopic device,
the first shape is one of a circle and an ellipse, and
the second shape is the other of the circle and the ellipse.

2. The image processing device according to claim 1, wherein the circuitry is configured to detect the plurality of boundary points based on a luminance value of a pixel.

3. The image processing device according to claim 2, wherein the circuitry is configured to detect the plurality of boundary points using two rectangular filters arranged to be spaced by a predetermined number of pixels.

4. The image processing device according to claim 2, wherein the circuitry is configured to detect the plurality of boundary points based on standard deviation of the luminance value.

5. The image processing device according to claim 4, wherein the standard deviation is calculated from a relational expression between the luminance value and the standard deviation, the relational expression being determined in advance.

6. The image processing device according to claim 1,
wherein the circuitry includes a central processing unit (CPU) and a graphics processing unit (GPU),
wherein one of the CPU and the GPU is configured to detect the plurality of boundary points, and
wherein the other of the CPU and the GPU is configured to estimate the shape of the boundary.

7. An image processing method comprising:
acquiring an image from an image sensor;
detecting a plurality of boundary points between a first region including a subject to be observed and a second region that does not include the subject in the image;
estimating a shape of a boundary between the first region and the second region based on the detected plurality of boundary points as a first shape;
deleting boundary points of the plurality of boundary points that fall within the first shape;
estimating the shape of the same boundary between the same first region and the same second region based on remaining boundary points of the plurality of boundary points as a second shape; and
displaying a mask shape based upon the second shape, wherein
the subject to be observed is a living body captured by an endoscopic device,
the first shape is one of a circle and an ellipse, and
the second shape is the other of the circle and the ellipse.

8. A non-transitory computer readable medium storing a program for causing a computer to execute:
acquiring an image from an image sensor;
detecting a plurality of boundary points between a first region including a subject to be observed and a second region that does not include the subject in the image;
estimating a shape of a boundary between the first region and the second region based on the detected plurality of boundary points as a first shape;
deleting boundary points of the plurality of boundary points that fall within the first shape;
estimating the shape of the same boundary between the same first region and the same second region based on remaining boundary points of the plurality of boundary points as a second shape; and
displaying a mask shape based upon the second shape, wherein
the subject to be observed is a living body captured by an endoscopic device,
the first shape is one of a circle and an ellipse, and
the second shape is the other of the circle and the ellipse.

* * * * *